(12) United States Patent
Gao et al.

(10) Patent No.: US 11,781,104 B2
(45) Date of Patent: Oct. 10, 2023

(54) ULTRA-MICROINJECTION DETECTION AND CONTROL DEVICE BASED ON LENSLESS IMAGING AND METHOD THEREOF

(71) Applicant: Harbin Institute of Technology, Harbin (CN)

(72) Inventors: Huijun Gao, Harbin (CN); Mingsi Tong, Harbin (CN); Xinghu Yu, Harbin (CN); Linqi Zhang, Harbin (CN)

(73) Assignee: Harbin Institute of Technology, Harbin (CN)

( * ) Notice: Subject to any disclaimer, the term of this patent is extended or adjusted under 35 U.S.C. 154(b) by 904 days.

(21) Appl. No.: 16/795,696

(22) Filed: Feb. 20, 2020

(65) Prior Publication Data

US 2020/0377843 A1 Dec. 3, 2020

(30) Foreign Application Priority Data

May 27, 2019 (CN) .......................... 201910446653.5

(51) Int. Cl.
| | | |
|---|---|---|
| *A61M 5/00* | (2006.01) | |
| *C12M 1/34* | (2006.01) | |
| *A61M 5/168* | (2006.01) | |
| *A61M 5/32* | (2006.01) | |
| *C12M 1/36* | (2006.01) | |

(Continued)

(52) U.S. Cl.
CPC ........ *C12M 41/44* (2013.01); *A61M 5/16831* (2013.01); *A61M 5/3286* (2013.01); *C12M 41/48* (2013.01); *C12N 15/89* (2013.01); *G01F 23/292* (2013.01); *A61M 2005/1588* (2013.01)

(58) Field of Classification Search
CPC .. C12M 41/44; C12M 41/48; A61M 5/16831; A61M 5/3286; C12N 15/89; G01F 23/292; G61M 2005/1588
See application file for complete search history.

(56) References Cited

U.S. PATENT DOCUMENTS

| | | | | |
|---|---|---|---|---|
| 2008/0124787 A1* | 5/2008 | Christmann | ........... | G02B 21/32 435/285.1 |
| 2017/0060242 A1* | 3/2017 | Gill | ...................... | G02B 5/1871 |

(Continued)

FOREIGN PATENT DOCUMENTS

| | | |
|---|---|---|
| CN | 101509801 A | 8/2009 |
| CN | 102614565 A | 8/2012 |

*Primary Examiner* — Khai M Nguyen
(74) *Attorney, Agent, or Firm* — Rimon PC

(57) ABSTRACT

The present invention provides an ultra-microinjection detection and control device based on lensless imaging and a method thereof. A lensless optical liquid level sensor is used to measure a change of a liquid level in an injection needle. A microinjection control unit is used to track the change of the liquid level and correct an injection pressure of the injection pump. Transmitted light generated by a parallel light source passes through a transparent glass tube of the injection needle. Then the transmitted light passes through a light filtering film to reduce the intensity of the parallel light source to a photosensitivity range of a micro linear array image sensor chip. Finally, the transmitted light enters the micro linear array image sensor chip, so that the micro linear array image sensor chip measures the change of the liquid level in the injection needle.

8 Claims, 3 Drawing Sheets

(51) Int. Cl.
*C12N 15/89* (2006.01)
*G01F 23/292* (2006.01)
*A61M 5/158* (2006.01)

(56) References Cited

U.S. PATENT DOCUMENTS

2018/0165823 A1* 6/2018 Ludwig ................ H04N 23/957
2019/0090801 A1* 3/2019 Rogers ................ A61B 5/4836

* cited by examiner

ULTRA-MICROINJECTION DETECTION AND CONTROL DEVICE BASED ON LENSLESS IMAGING AND METHOD THEREOF

RELATED APPLICATIONS

This application claims the benefit of priority under the Paris Convention from Chinese Application No. 201910446653.5 filed May 27, 2019, the disclosure of which is incorporated herein by reference in its entirety.

TECHNICAL FIELD

The present invention relates to a lensless imaging technology and an ultra-microinjection control technology for a microinjection system in the field of life sciences. In particular, the present invention relates to a new method for a closed-loop control of a microinjection pump by imaging a liquid level in a glass capillary injection needle by a linear array image sensor without a lens and measuring a position change of the liquid level. The method is mainly used for a real-time detection of a liquid level in a needle tube during microinjection of microorganisms such as embryos, cells and zebrafish larvae, so as to generate feedback to achieve precise control of an injection volume.

BACKGROUND

With the advancement of life science and technology, genetic, pharmacological and developmental research based on microorganisms such as embryos, cells, zebrafish larvae, nematodes and fruit flies has become a widely used research method. These experimental subjects are only a few micrometers to hundreds of micrometers in size. Therefore, microinjection using a glass capillary needle under a microscope is the most widely used method of injecting foreign substances such as genes and drugs into microorganisms. At present, in a common microinjection system, a needle holder is used to connect a glass capillary needle pulled by a needle puller to a microinjection pump for injection, as shown in FIG. 1. An operator places a sample under a microscope, manipulates the needle holder to penetrate the glass needle into the experimental subject, and starts the injection pump to complete injection. A tip of the glass capillary needle generally has a diameter of 5-20 μm. A straight section of the glass needle generally has a diameter of about 1 mm. The inner diameter has different specifications, and a commonly used inner diameter is 0.5 mm. For an injection volume below 20 nL, a pneumatic microinjection pump is generally used as a driver. The use of pneumatic pumps for microinjection is currently the most mature injection method. Internationally mature commercial microinjection pumps adjust a single-injection volume by adjusting a holding pressure, an injection pressure and an injection time. The holding pressure is used to overcome the effects of a capillary force and a gravity of a liquid in the glass needle, etc., so as to maintain a liquid level balance in the glass needle. When injecting, the injection pump overcomes the capillary force and breaks the liquid level balance by the injection pressure, thereby driving the liquid level forward to achieve injection. An actual injection volume V is equal to:

$$V = v \cdot d \cdot t \quad (1)$$

where, v is a moving speed of the liquid level, d is an inner diameter of the capillary tube, and t is an injection time.

FIG. 1 is a schematic diagram of the microinjection system. As shown in the figure, due to a narrow field of view of the microscope and a short imaging focal length, it is not possible to observe the change of the liquid level in the glass needle in real time through the microscope during the injection process. Generally, the parameters of the injection pump can only be adjusted by experience before an experiment. The injection parameters are related to the length, shape, opening size of the glass needle (as shown in FIG. 2) and the viscosity of the injection liquid, etc. Therefore, it takes a lot of time to test the injection parameters before each experiment. Meanwhile, during the injection process, the changes of the capillary force, the liquid level and an external environment will cause a significant change in the injection parameters. Thus, during the experiment, the injection volume will usually have a large error. When a macromolecular agent is injected, a blockage difficult to find by an experimenter often occurs, which leads to poor uniformity of injection between different samples. This problem severely restricts the development of large-scale, high-throughput life science experiments, and is one of the major problems to be solved urgently.

The key to solving this problem is to add a sensing device that can sense the position change of the liquid level in the glass needle. Microinjection requires nanoliter control of the injection volume, which causes only a few micrometers of liquid level change. Therefore, the measurement of the liquid level can only be performed by adding a microscopic device. In a general optical system, light reflected (or emitted) by an object needs to be projected through a lens system onto a complementary metal-oxide-semiconductor (CMOS) or charge coupled device (CCD) image sensor chip for imaging. In order to ensure the clarity of imaging, a certain distance must be maintained between the object and the lens as well as between the lens and the sensor chip, which requires the imaging system to have a large volume. However, in the micromanipulation system, due to the limitation of the space structure, it is unrealistic to add an additional microscope for liquid level observation.

Therefore, it is necessary to develop an ultra-micro liquid level sensing and control device to measure the liquid level change in the glass needle in real time and adjust the injection parameters of the microinjection pump on line through a control algorithm, without interfering in space with other instruments such as the microscope and a robotic arm.

SUMMARY

The present invention is to solve the problem that the prior art lacks a device capable of accurately detecting a position change of a liquid level in a glass capillary needle and accurately controlling a volume of an injection liquid. The present invention provides an ultra-microinjection detection and control device based on lensless imaging and a method thereof.

An ultra-microinjection detection and control device based on lensless imaging is provided, where the device includes an injection pump and a needle holder e; the needle holder e is used to hold an injection needle c; the injection pump is used to provide power needed for injection; the device further includes a lensless optical liquid level sensor and a microinjection control unit.

The lensless optical liquid level sensor is arranged on an outer wall of the injection needle c, for measuring a change of a liquid level in the injection needle c.

The microinjection control unit is arranged on the needle holder e, for tracking a change of the liquid level and correcting an injection pressure of the injection pump, so as to stabilize the liquid level in the injection needle c.

The lensless optical liquid level sensor includes a micro linear array image sensor chip 5, a light filtering film 1, a parallel light source 4 and a holding housing 6.

The parallel light source 4 is arranged on an outer side wall of the injection needle c. The light filtering film 1 is arranged on an outer side wall of the injection needle c and located on a transmitted plane of the parallel light source 4. The micro linear array image sensor chip 5 is arranged on an outer surface of the light filtering film 1. The holding housing 6 encloses the micro linear array image sensor chip 5, the light filtering film 1 and the parallel light source 4.

Transmitted light generated by the parallel light source 4 passes through a transparent glass tube of the injection needle c. Then the transmitted light passes through the light filtering film 1 to reduce the intensity of the parallel light source 4 to a photosensitivity range of the micro linear array image sensor chip 5. Finally, the transmitted light enters the micro linear array image sensor chip 5, so that the micro linear array image sensor chip 5 measures the change of the liquid level in the injection needle c.

A method for implementing the ultra-microinjection detection and control device based on lensless imaging is provided, where the method includes the following steps:

step 1, the light emitted by the parallel light source 4 passes through the transparent glass injection needle c and enters the micro linear array image sensor chip 5 via the light filtering film 1; the liquid level in the injection needle c presents a virtual image on the micro linear array image sensor chip 5;

step 2: the microinjection control unit calculates an injection parameter of a liquid according to the virtual image; and step 3: the microinjection control unit corrects a pressure of the injection pump according to a minimum injection volume, so as to stabilize the injection liquid in the injector.

The present invention has the following beneficial effects.

The present application uses the glass capillary needle as an imaging object. The imaging object directly adheres to a surface of the sensor chip without the use of a lens. The light generated by the parallel light source passes through the glass needle to enter the micro linear array image sensor chip. As the refraction and scattering of the light passing through the liquid and passing through the air are different, there is a difference in the brightness on the micro linear array image sensor chip. Generally speaking, the light has a bright image on the micro linear array image sensor chip after passing through the liquid and a dark image after passing through the air. In this process, the light intensity in the air is smaller than a saturation intensity on the micro linear array image sensor chip. Since the light enters the micro linear array image sensor chip without being focused by a lens, the liquid level in the glass needle presents a virtual image on the micro linear array image sensor chip. The change of the liquid level can be measured through a gray change of the virtual image. A relationship between the light intensity and displacement of the liquid level is shown in FIG. 5. Then, the change of the liquid level is collected to correct the injection pressure of the injection pump, so that the injection liquid in the injection needle is stabilized.

Compared with the prior art, the present application has the following advantages.

1. The present application uses a lensless imaging method to enable microscopic measurement in a very compact volume. Taking Implementation Scheme 1 as an example, the sensor volume can be controlled within 15 mm×7 mm×7 mm, so that the sensor can be directly held on the injection needle without affecting the microinjection operation. A traditional optical microscope system requires a complex light path and light source structure. Its volume and weight are hundreds to thousands of times larger than those of the sensor established by the present invention, and cannot be used for the measurement of the liquid level in the injection needle.

2. The present application can realize ultra-high-precision measurement of the liquid level change, and provide high-precision feedback for the ultra-micro control of microinjection. In Implementation Scheme 1, a theoretical minimum resolution of the present application can reach 3.4 pL, which cannot be achieved by the prior art of liquid level measurement.

3. The present application has a strong anti-interference ability. As the micro linear array image sensor chip adopts optical measurement and a closed light source environment, its signal is not easily affected by external interference. Other micro-droplet measurement methods, for example, droplet sensing by using a capacitor, cannot achieve high-precision measurement. As the capacitor has a very small change of capacitance, a sensing signal of the capacitor is extremely susceptible to external factors such as electromagnetic field and power supply fluctuations and the capacitor's own edge effect.

4. The present application has the characteristics of simple structure, low cost and high technical maturity, etc. The devices used in this application are all mature devices in the industrial field. The devices cost only a few thousand yuan by small-batch production, and are suitable to various types of commercial pneumatic microinjection pumps. They are mature and reliable in the scheme. Compared with some piezoelectric ceramic-driven ultra-microinjection methods that are currently under research, the present application has obvious advantages in cost and reliability.

5. The present application does not generate a "dead zone" in the microinjection instrument. The dead zone is an area of air bubbles that cannot be removed. The volume of a remaining air bubble continuously changes during the injection process, which seriously affects the control accuracy of the injection volume. The present application adopts noninvasive measurement, which does not require an experimenter to change a general operation habit or affect conventional methods of exhausting and liquid filling. However, some similar methods driven by piezoelectric ceramics use invasive measurement and drive, which are prone to generate a "dead zone" in the structure.

DETAILED DESCRIPTION

Figure 1:
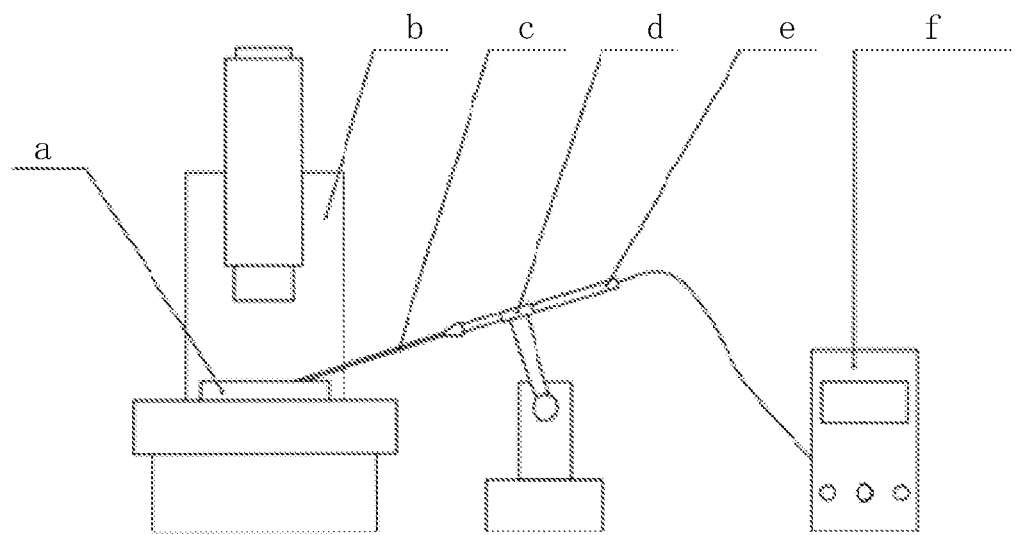
FIG. 1 is a schematic structural diagram of a conventional microinjection system, where reference numeral a represents a petri dish; reference numeral b represents a microscope; reference numeral c represents an injection needle; reference numeral d represents a robotic arm; reference numeral e represents a needle holder; reference numeral f represents an injection pump, which can be implemented by a pneumatic microinjection pump.
Figure 2:
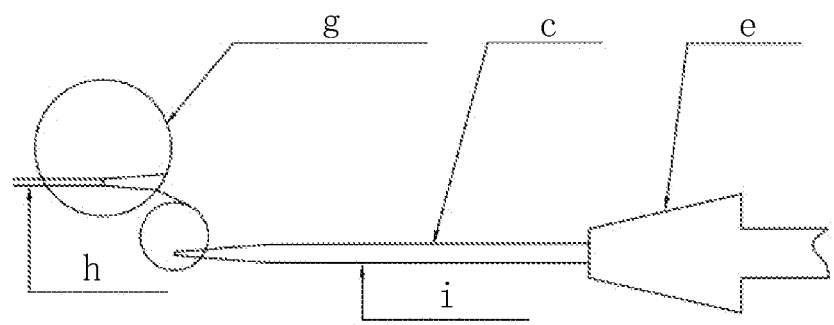
FIG. 2 is a detail drawing of an injection needle in FIG. 1, where reference numeral g represents a detail drawing of a needle tip; reference numeral h represents an outer diameter of the needle tip, which is 20 μm; reference numeral i represents an outer diameter of a needle tube, which is 1,000 μm.
Figure 3:
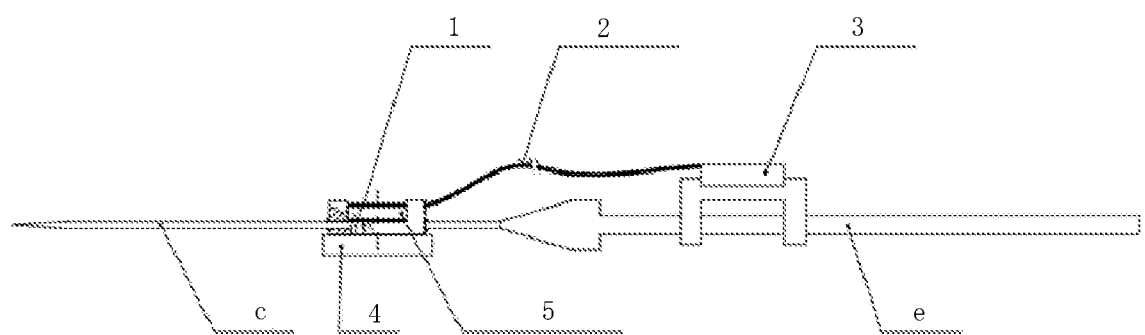
FIG. 3 is a schematic structural diagram of an ultra-microinjection detection and control device based on lensless imaging according to Specific Implementation 1.

Specific Implementation 1: This implementation is described in detail with reference to FIG. 3 and FIG. 4. This implementation provides an ultra-microinjection detection and control device based on lensless imaging, where the device includes an injection pump and a needle holder e; the needle holder e is used to hold an injection needle c; the injection pump is used to provide pressure needed for injection; the device further includes a lensless optical liquid level sensor and a microinjection control unit.

The lensless optical liquid level sensor is arranged on an outer wall of the injection needle c, for measuring a change of a liquid level in the injection needle c.

The microinjection control unit is arranged on the needle holder e, for tracking a change of the liquid level and correcting an injection pressure of the injection pump, so as to stabilize the liquid level in the injection needle c.

The lensless optical liquid level sensor includes a micro linear array image sensor chip 5, a light filtering film 1, a parallel light source 4 and a holding housing 6.

The parallel light source 4 is arranged on an outer side wall of the injection needle c. The light filtering film 1 is arranged on an outer side wall of the injection needle c and located on a transmitted plane of the parallel light source 4. The micro linear array image sensor chip 5 is arranged on an outer surface of the light filtering film 1. The holding housing 6 encloses the micro linear array image sensor chip 5, the light filtering film 1 and the parallel light source 4.

Transmitted light generated by the parallel light source 4 passes through a transparent glass tube of the injection needle c. Then the transmitted light passes through the light filtering film 1 to reduce the intensity of the parallel light source 4 to a photosensitivity range of the micro linear array image sensor chip 5. Finally, the transmitted light enters the micro linear array image sensor chip 5, so that the micro linear array image sensor chip 5 measures the change of the liquid level in the injection needle c.

In this implementation, the micro linear array image sensor chip 5 is held on the glass injection needle. The micro linear array image sensor chip 5 is connected to the microinjection control unit through a flexible circuit board. The microinjection control unit can be arranged on the needle holder and a micromanipulator, etc.

The light filtering film can reduce an incident light intensity in a specific spectral range at a specific ratio. The function of the light filtering film is to eliminate the interference of external stray light on the sensor, and reduce the intensity of the parallel light source to the photosensitivity range of the image sensor.

The parallel light source is composed of a light-emitting diode (LED) element, an optical fiber and a light homogenizing film, providing homogeneous and stable transmitted light.

Figure 4:
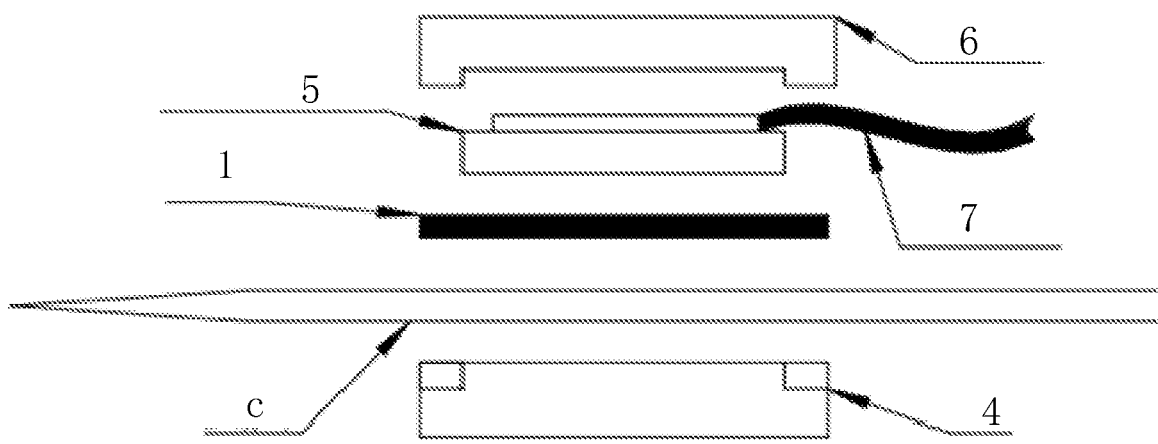
FIG. 4 is an exploded view of a lensless optical liquid level sensor in FIG. 3.
Figure 5:
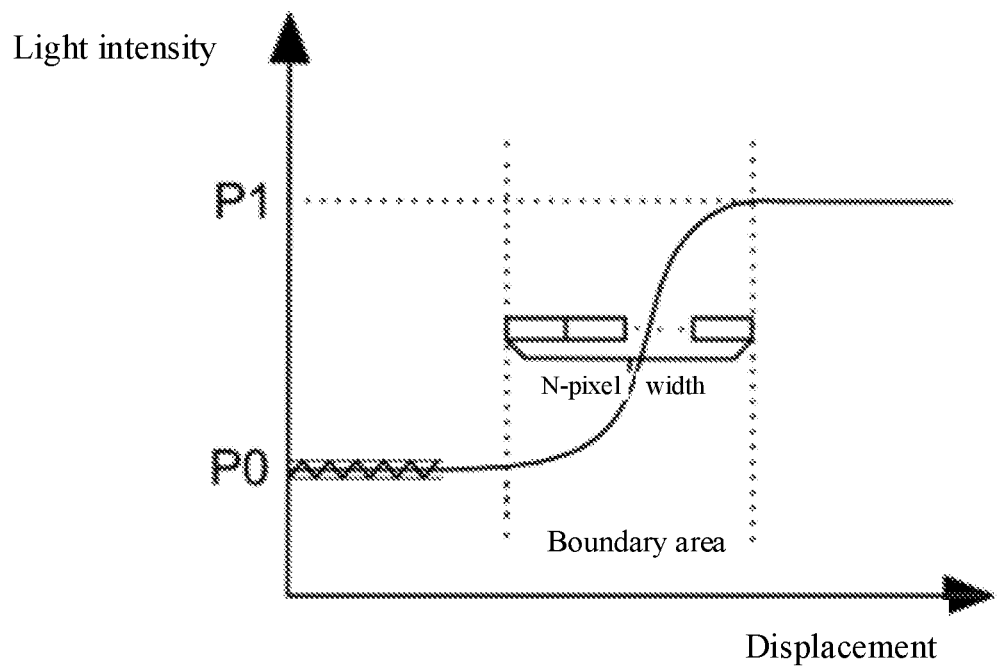
FIG. 5 is a schematic diagram showing a relationship between a light intensity collected by a micro linear array image sensor chip and displacement.
Figure 6:
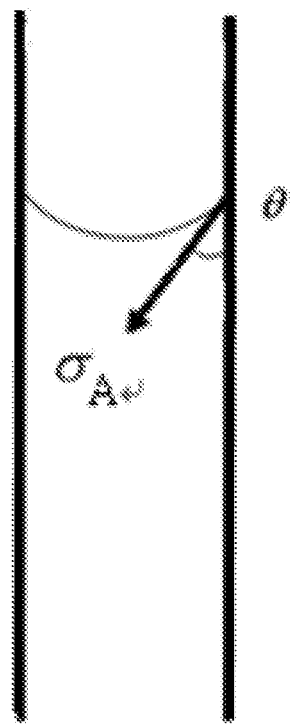
FIG. 6 is a schematic diagram showing a capillary force of a liquid level in an injection needle.
Figure 7:
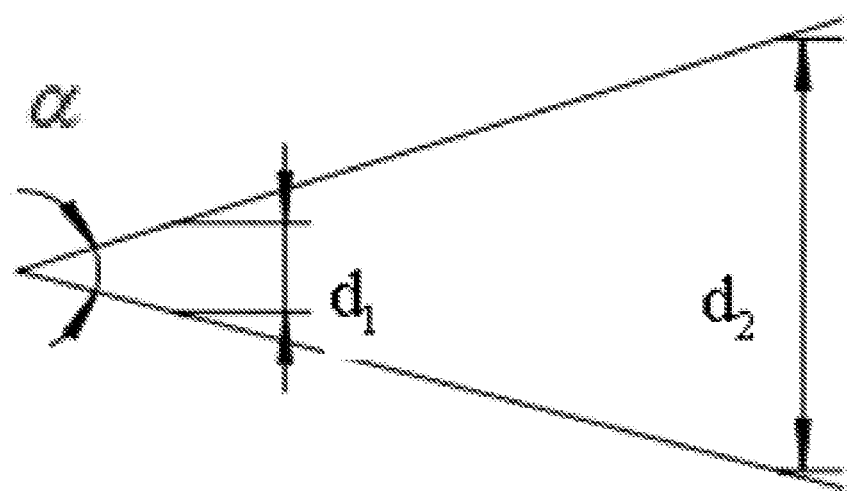
FIG. 7 is a needle tip fluid model of an injection needle.

The holding housing is a structure integrating the micro linear array image sensor chip, the light filtering film and the parallel light source, and creating a closed environment to reduce the entry of external light. The holding housing also has a rubber structure for providing resistance to ensure stable measurement when held on the glass needle. The above structure is shown in FIG. 4.

The control unit mainly completes an image acquisition and processing algorithm, a flow control algorithm and a communication program, etc. The hardware can be assumed by computing chips such as a single-chip computer, a digital signal processor DSP and a field programmable gate array FPGA.

EMBODIMENT 1

In the present invention, the micro linear array image sensor chip may use an S10226 linear complementary metal-oxide-semiconductor transistor (CMOS) image sensor produced by Hamamatsu as a sensor chip. This sensor chip has 12 sensing bits. In a photosensitive area, a single pixel has a size of 7×125 μm, and a linear array has a total of 1,024 pixels. The photosensitive area has a total length of 8 mm and overall dimensions of 9.1 mm×2.4 mm×1.6 mm. A surface of the sensor is covered with a 90% light filtering film. The sensor is provided with an external light source composed of a LED element and an optical fiber, with a light intensity of about 150 lux. The glass injection needle can be pulled from a glass capillary tube with an outer diameter of 1 mm and an inner diameter of 0.5 mm. The pneumatic microinjection pump can be used with a FemtoJet 4i picoliter upgrade microinjection pump produced by Eppendorf.

In this embodiment, it is assumed that the light passing through the liquid level can saturate the sensor pixels, the light passing through the air does not reach a threshold of the sensor after passing through the light filtering film, and a boundary of the liquid level has a light intensity difference of 4,096. An electrical noise fluctuation, which is set to 10%, is substituted into Formula 1 to obtain a theoretical minimum liquid level resolution as follows:

$$\Delta x = \frac{N \cdot a}{(P_1 - P_0)\varepsilon_0} = \frac{7\ \mu m}{4096 \times 10\%} = 0.017\ \mu m, \quad \text{Formula 1}$$

Δx is substituted into Formula 2:

$$V_{min} = \frac{1}{4} \cdot \pi d^2 \Delta x, \quad \text{Formula 2}$$

The minimum injection volume is calculated to be 3.4 pL. The resolution exceeds the requirements of the minimum injection volume of the microinjection pump and an injection volume of a general life science experiment. Therefore, the resolution meets the need of actual use.

For an injection needle having an inner diameter of 0.5 mm, the boundary of the liquid level is about 35 μm in width. Therefore, when the S10226 sensor is used, a maximum sensing range of the sensor in terms of liquid level is (8 mm−2×0.035 mm)=7.93 mm, which is equal to a maximum range of 1.56 μL in terms of liquid volume. By calculating based on a single-injection volume of 2 nL in a general experiment, the volume of the liquid filled once in the present application can be used for 780 injections, which meets a continuous injection requirement of most experiments.

Specific Implementation 2: This implementation further describes the ultra-microinjection detection and control device based on lensless imaging as described in Specific Implementation 1. In this implementation, the parallel light source 4 includes a LED element, an optical fiber and a light homogenizing film. The LED element, the optical fiber and the light homogenizing film are arranged in order from outside to inside.

Specific Implementation 3: This implementation further describes the ultra-microinjection detection and control device based on lensless imaging as described in Specific Implementation 1. In this implementation, the control unit includes a driver circuit 3 and a flexible circuit board 2. The driver circuit 3 is arranged on the needle holder e, and the driver circuit 3 is connected to the micro linear array image sensor chip 5 through the flexible circuit board 2. The flexible circuit board 2 is used to acquire measurement information of the micro linear array image sensor chip 5, and correct the injection pressure of the injection pump based on the information. The driver circuit 3 is used to drive the injection pump according to the injection pressure sent by the flexible circuit board 2.

Specific Implementation 4: This implementation further describes the ultra-microinjection detection and control device based on lensless imaging as described in Specific Implementation 1. In this implementation, the micro linear array image sensor chip 5 is an image sensor chip with only one or a few rows of photosensitive units in a y direction and hundreds or thousands of photosensitive units in an x direction.

In this implementation, the linear array image sensor chip is an image sensor chip with only one or a few rows of photosensitive units in a y direction and hundreds or thousands of photosensitive units in an x direction. A length of the sensor chip in the x direction determines the maximum range of liquid level measurement. A size of the photosensitive unit in the x direction is directly proportional to a measurement accuracy of the sensor. A size of the photosensitive unit in the y direction is inversely proportional to a need of the sensor for the brightness of the light source. The sensitivity of the photosensitive unit to light intensity is within a certain range, and the measured light intensity must be within this range.

Specific Implementation 5: A method for implementing the ultra-microinjection detection and control device based on lensless imaging as described in Specific Implementation 1, where the method includes the following steps:

step 1, the light emitted by the parallel light source 4 passes through the transparent glass injection needle c and enters the micro linear array image sensor chip 5 via the light filtering film 1; the liquid level in the injection needle c presents a virtual image on the micro linear array image sensor chip 5;

step 2: the microinjection control unit obtains a minimum injection volume of the liquid according to the virtual image; and step 3: the microinjection control unit corrects a pressure of the injection pump according to the minimum injection volume, so as to stabilize the injection liquid in the injector.

Specific Implementation 6: This implementation further describes the method for implementing the ultra-microinjection detection and control device based on lensless imaging as described in Specific Implementation 5. In this implementation, the minimum injection volume of the liquid is:

a theoretical minimum resolution $\Delta x$ of the micro linear array image sensor chip 5 is expressed as follows:

$$\Delta_x = \frac{N \cdot a}{(p_1 - p_0)\varepsilon_0}, \quad \text{Formula 1}$$

where, $P_0$ and $P_1$ are binary representations of a light intensity in the liquid and in the air; a is a single-pixel length; N is a number of pixels passing from a minimum light intensity $P_0$ to a maximum light intensity $P_1$ through a boundary area of the liquid level; according to the theoretical minimum resolution $\Delta x$ of the micro linear array image sensor chip 5, the minimum injection volume of the liquid is as follows:

$$V_{min} = \tfrac{1}{4}\pi d^2 \Delta x, \quad \text{Formula 2}$$

where, d is an inner diameter of the injection needle; $V_{min}$ is a minimum injection volume of the liquid in the injection needle.

In this implementation, a signal acquired by the micro linear array image sensor chip includes a noise fluctuation of the light source and the sensor. Therefore, the light intensity resolution represented by $(P_1 - P_0)$ needs to be multiplied by an error coefficient $\varepsilon_0$, and the value needs to be determined based on a noise width of the sensor.

Specific Implementation 7: This implementation further describes the method for implementing the ultra-microinjection detection and control device based on lensless imaging as described in Specific Implementation 6. In this implementation, in step 3, the microinjection control unit corrects a pressure of the injection pump according to the following formula:

according to an equation for a liquid level balance in the injection needle c:

$$F_b = F_c + F_G + F_a, \quad \text{Formula 3}$$

a balance pressure $F_b$ of the injection pump is obtained; where, $F_c$ is a capillary force generated by a needle end to the liquid in the injection needle;

$F_G$ is a vertical component of a gravity of the liquid in the injection needle during injection;

$F_a$ is an ambient pressure.

The liquid in the injection needle c has a capillary force at the needle tip and the needle end. In an actual application, the needle tip will be immersed in water or a liquid mixed with water, so that the capillary force at the needle tip disappears. Therefore, only the capillary force $F_c$ generated by the needle end to the liquid in the injection needle remains. The capillary force $F_c$ at the boundary is:

$$F_c = 2\pi r \sigma_A \cos \theta, \quad \text{Formula 4}$$

the vertical component $F_G$ of the gravity of the liquid in the injection needle during injection is:

$$F_G = \pi r^2 \rho g h \cdot \sin \beta, \quad \text{Formula 5}$$

where, $\sigma_A \cos \theta$ is a tensile force acting on a water column on a three-phase perimeter of a unit length within the capillary tube, measured by an experiment; $\theta$ represents an angle between a concave surface of the liquid in the glass capillary tube and a wall of the glass tube; r is an inner radius of the injection needle; $\beta$ is an angle between the injection needle and a horizontal plane during an actual injection.

The microinjection control unit corrects the balance pressure of the injection pump according to the minimum injection volume, so as to stabilize the injection liquid in the injector.

Specific Implementation 8: This implementation further describes the method for implementing the ultra-microinjection detection and control device based on lensless imaging as described in Specific Implementation 7. In this implementation, the stability of the injection liquid in the injector refers to a balance between the injection pressure and a liquid flow of the injection needle.

The injection pressure and the liquid flow satisfy a relationship as follows.

During the injection, a relationship between an injection pressure and a flow of the needle tip is calculated by using micro-hydrodynamics. The flow Q of the needle tip is estimated by a Poisson equation:

$$Q = \frac{d^4 p}{128 \, \mu L}, ,$$ Formula 7 where, p is an injection pressure, $\mu$ is a dynamic viscosity, and L is a length of a tube.

The needle tip is simplified to a cross section of a tube with a uniformly varying cross section, $d=2 \tan \theta$. The cross section is derived, and the flow in a tapered tube satisfies $$\frac{dp}{dx} = const\theta.$$

The relationship between the pressure and the flow is:

$$\int_{d_1}^{d_2} \frac{64 Q u}{\pi \tan \alpha d^4} d(d), ,$$ Formula 8 where, $d_1$ and $d_2$ are outlet and inlet diameters of the needle tip, respectively; $\alpha$ is an included angle of the needle tip.

From the above derivation, the corresponding injection pressure and injection time can be calculated. When the control unit controls the injection pump to perform the injection operation, the control unit tracks the change of the liquid level to monitor a change in the injection volume. In this way, the control unit corrects the injection parameters and prompts the occurrence of common faults such as blockage.

What is claimed is:

1. An ultra-microinjection detection and control device based on lensless imaging, wherein the device comprises an injection pump and a needle holder (e); the needle holder (e) is used to hold an injection needle (c); the injection pump is used to provide power needed for injection; the device further comprises a lensless optical liquid level sensor and a microinjection control unit;

the lensless optical liquid level sensor is arranged on an outer wall of the injection needle (c), for measuring a change of a liquid level in the injection needle (c);

the microinjection control unit is arranged on the needle holder (e), for detecting the change of the liquid level and correcting an injection pressure of the injection pump, so as to stabilize the liquid level in the injection needle (c);

the lensless optical liquid level sensor comprises a micro linear array image sensor chip (5), a light filtering film (1), a parallel light source (4) and a holding housing (6);

the parallel light source (4) is arranged on an outer side wall of the injection needle (c); the light filtering film (1) is arranged on an outer side wall of the injection needle (c) and located on a transmitted plane of the parallel light source (4); the micro linear array image sensor chip (5) is arranged on an outer surface of the light filtering film (1); the holding housing (6) encloses the micro linear array image sensor chip (5), the light filtering film (1) and the parallel light source (4);

transmitted light generated by the parallel light source (4) passes through a transparent glass tube of the injection needle (c); then the transmitted light passes through the light filtering film (1) to reduce the intensity of the parallel light source (4) to a photosensitivity range of the micro linear array image sensor chip (5); finally, the transmitted light enters the micro linear array image sensor chip (5), so that the micro linear array image sensor chip (5) measures the change of the liquid level in the injection needle (c).

2. The ultra-microinjection detection and control device based on lensless imaging according to claim 1, wherein the parallel light source (4) comprises a light-emitting diode (LED) element, an optical fiber and a light homogenizing film; the LED element, the optical fiber and the light homogenizing film are arranged in order from outside to inside.

3. The ultra-microinjection detection and control device based on lensless imaging according to claim 1, wherein the control unit comprises a driver circuit (3) and a flexible circuit board (2); the driver circuit (3) is arranged on the needle holder (e), and the driver circuit (3) is connected to the micro linear array image sensor chip (5) through the flexible circuit board (2); the flexible circuit board (2) is used to acquire measurement information of the micro linear array image sensor chip (5), and correct the injection pressure of the injection pump based on the information; the driver circuit (3) is used to drive the injection pump according to the injection pressure sent by the flexible circuit board (2).

4. The ultra-microinjection detection and control device based on lensless imaging according to claim 1, wherein the micro linear array image sensor chip (5) is an image sensor chip with only one or a few rows of photosensitive units in a y direction and hundreds or thousands of photosensitive units in an x direction.

5. A method for implementing the ultra-microinjection detection and control device based on lensless imaging according to claim 1, wherein the method comprises the following steps:

step 1, the light emitted by the parallel light source (4) passes through the transparent glass injection needle (c) and enters the micro linear array image sensor chip (5) via the light filtering film (1); the liquid level in the injection needle (c) presents a virtual image on the micro linear array image sensor chip (5);

step 2: the microinjection control unit obtains a minimum injection volume of a liquid according to the virtual image; and step 3: the microinjection control unit corrects a pressure of the injection pump according to the minimum injection volume, so as to stabilize the injection liquid in the injector.

6. The method for implementing the ultra-microinjection detection and control device based on lensless imaging according to claim 5, wherein the minimum injection volume of the liquid is as follows:

a theoretical minimum resolution $\Delta x$ of the micro linear array image sensor chip (5) is expressed as follows:

$$\Delta x = \frac{N \cdot a}{(P_1 - P_0)\varepsilon_0}, \qquad \text{Formula 1}$$

wherein, $P_0$ and $P_1$ are binary representations of a light intensity in the liquid and in the air; a is a single-pixel length; N is a number of pixels passing from a minimum light intensity $P_0$ to a maximum light intensity $P_1$ through a boundary area of the liquid level;

according to the theoretical minimum resolution $\Delta x$ of the micro linear array image sensor chip (5), the minimum injection volume of the liquid is as follows:

$$V_{min} = \tfrac{1}{4} \cdot \pi d^2 \Delta x, \qquad \text{Formula 2}$$

wherein, d is an inner diameter of the injection needle; $V_{min}$ is a minimum injection volume of the liquid in the injection needle.

7. The method for implementing the ultra-microinjection detection and control device based on lensless imaging according to claim 6, wherein in step 3, the microinjection control unit corrects a pressure of the injection pump according to the following formula:

according to an equation for a liquid level balance in the injection needle (c):

$$F_b = F_c + F_G + F_a, \qquad \text{Formula 3}$$

a balance pressure $F_b$ of the injection pump is obtained, wherein, $F_c$ is a capillary force generated by a needle end to the liquid in the injection needle; $F_G$ is a vertical component of a gravity of the liquid in the injection needle during injection; $F_a$ is an ambient pressure;

the liquid in the injection needle (c) has a capillary force at the needle tip and the needle end; in an actual application, the needle tip will be immersed in water or a liquid mixed with water, so that the capillary force at the needle tip disappears; therefore, only the capillary force $F_c$ generated by the needle end to the liquid in the injection needle remains; the capillary force $F_c$ at a boundary is:

$$F_c = 2\pi r \sigma_A \cos\theta, \qquad \text{Formula 4}$$

the vertical component $F_G$ of the gravity of the liquid in the injection needle during injection is:

$$F_G = \pi r^2 \rho g h \cdot \sin\beta, \qquad \text{Formula 5}$$

wherein, $\sigma_A \cos\theta$ is a tensile force acting on a water column on a three-phase perimeter of a unit length within the capillary tube, measured by an experiment; $\theta$ represents an angle between a concave surface of the liquid in the glass capillary tube and a wall of the glass tube; r is an inner radius of the injection needle; $\beta$ is an angle between the injection needle and a horizontal plane during an actual injection;

the microinjection control unit corrects the balance pressure of the injection pump according to the minimum injection volume, so as to stabilize the injection liquid in the injector.

8. The method for implementing the ultra-microinjection detection and control device based on lensless imaging according to claim 7, wherein the stability of the injection liquid in the injector refers to a balance between the injection pressure and a liquid flow of the injection needle;

the injection pressure and the liquid flow satisfy:

during the injection, a relationship between an injection pressure and a flow of the needle tip is calculated by using micro-hydrodynamics; the flow Q of the needle tip is estimated by a Poisson equation:

$$Q = \frac{d^4 p}{128\, \mu L}, \qquad \text{Formula 6}$$

wherein, p is an injection pressure, $\mu$ is a dynamic viscosity, and L is a length of a tube;

the needle tip is simplified to a cross section of a tube with a uniformly varying cross section, $d = 2 \tan\theta$; the cross section is derived, and the flow in a tapered tube satisfies $$\frac{dp}{dx} = const\theta;$$

the relationship between the pressure and the flow is:

$$\int_{d_1}^{d_2} \frac{64 Q u}{\pi \tan\alpha d^4} d(d), \qquad \text{Formula 7}$$

wherein, $d_1$ and $d_2$ are outlet and inlet diameters of the needle tip, respectively; $\alpha$ is an included angle of the needle tip.

* * * * *